(12) United States Patent
Girshovich et al.

(10) Patent No.: US 8,287,681 B2
(45) Date of Patent: Oct. 16, 2012

(54) METHOD FOR MAKING COMPOSITE ARTICLES WITH ARTIFICIAL DEFECTS

(75) Inventors: Simon Girshovich, Kfar Saba (IL); Reuven Feldman, Ramat-Gan (IL)

(73) Assignee: Israel Aerospace Industries Ltd., Lod (IL)

( * ) Notice: Subject to any disclaimer, the term of this patent is extended or adjusted under 35 U.S.C. 154(b) by 773 days.

(21) Appl. No.: 11/197,114

(22) Filed: Aug. 4, 2005

(65) Prior Publication Data

US 2007/0028661 A1   Feb. 8, 2007

(51) Int. Cl.
*B29C 65/00* (2006.01)
*B32B 37/00* (2006.01)

(52) U.S. Cl. .................. 156/252; 156/307.1; 156/324.4

(58) Field of Classification Search .................. 156/252, 156/307.1, 307.3, 307.4, 307.5, 307.7, 324.4, 156/64; 73/1.01, 1.86
See application file for complete search history.

(56) References Cited

U.S. PATENT DOCUMENTS

| | | | |
|---|---|---|---|
| 4,173,139 A | | 11/1979 | Conn |
| 4,746,718 A | * | 5/1988 | Gardner et al. .................. 528/98 |
| 4,791,154 A | * | 12/1988 | Corley et al. .................. 523/456 |
| 4,856,335 A | * | 8/1989 | Tornberg .......................... 73/597 |
| 5,128,198 A | * | 7/1992 | Dyksterhouse et al. ........ 442/59 |
| 5,292,475 A | * | 3/1994 | Mead et al. ..................... 264/257 |
| 5,470,649 A | * | 11/1995 | Farley ............................ 442/238 |
| 5,629,497 A | * | 5/1997 | Sato et al. ...................... 174/255 |
| 6,027,786 A | * | 2/2000 | Ford .............................. 428/137 |
| 6,379,799 B1 | * | 4/2002 | Almen ........................... 428/413 |
| 6,448,509 B1 | * | 9/2002 | Huemoeller ................... 174/262 |
| 6,452,285 B1 | | 9/2002 | McCarthy et al. |
| 2002/0066318 A1 | | 6/2002 | Dubois |
| 2005/0194724 A1 | * | 9/2005 | Krogager et al. .............. 264/510 |

FOREIGN PATENT DOCUMENTS

| | | |
|---|---|---|
| JP | 51-265565 A | 11/1986 |
| JP | 10-227773 A | 8/1998 |
| JP | 11037981 | 2/1999 |

OTHER PUBLICATIONS

Denney, J.J., "Fatigue Response of Cracked Aluminum Panel With Partially Bonded Composite Patch", Air Force Inst. of Tech., Master's Thesis, Wright-Patterson AFB, Ohio, Dec. 1995, p. 40, AD-A306 361/7.
Roach, D., et al., "Development of Composite Honeycomb and Solid Laminate Reference Standards to Aid Aircraft Inspections", NDT. net, Mar. 1999, vol. 4, No. 3, pp. 1-2.
Wiggenraad, J.F.M., et al., "Damage Propagation in Composite Structural Elements, Analysis and Experiments on Structures", Conference Proceedings, National Aerospace Lab., Amsterdam (Netherlands), May 1996, pp. 20-22, PB2000-100069.
European Search Report of Jul. 7, 2010 for European Application No. EP 06016197.

* cited by examiner

*Primary Examiner* — John Goff
(74) *Attorney, Agent, or Firm* — Browdy and Neimark, PLLC

(57) ABSTRACT

The present invention concerns a composite article comprising a plurality of layers, wherein at least one of the layers is a defective polymeric layer. The defective polymeric layer has at least one artificial defect, in the form of a volume of air confined by walls made of said defective polymeric layer, and by layers adjacent thereto. The invention further provides the use of a composite article for calibrating equipment and a method for making such a composite article.

7 Claims, 2 Drawing Sheets

METHOD FOR MAKING COMPOSITE ARTICLES WITH ARTIFICIAL DEFECTS

FIELD OF THE INVENTION

This invention relates to composite articles with artificial defects and their use in damage tolerance tests and as calibration standards in non-destructive testing.

BACKGROUND OF THE INVENTION

A composite article is an article made of one or more composite materials, e.g. materials comprising two or more components. One component is a fibre (continuous or chopped), while another component (also called a matrix) is a polymeric resin that binds the fibres together.

Composite article serve in many fields and may be found as building materials in armour plates, in aircrafts, and many others.

Before a composite article is put in service, it is important to evaluate its damage tolerance, that is, in what way defects of predetermined sizes might affect the article's stress limit, life time, etc. For this end, model articles with artificial defects are made, and their ability to stand stresses is tested.

Composite articles with artificial defects are also necessary in nondestructive testing, which is a technology regularly used for detecting defects that may be detrimental to the functioning of such articles in service. Defects appear in composite articles during manufacture, if the manufacturing protocol is not strictly followed, or during service of the article, due to stresses and environmental conditions, under which it serves. The main kind of defects are separation of layers (also called delaminations or debonding) and small voids dissipated through the entire volume in the article or a portion thereof, which is much larger than the single void. Such defect is also called porosity.

All real defects are air filled.

There are well-established requirements to detect defects of determined size (specific size depend on the specific application of the composite), and in order to do so, calibration standards with defects of predetermined size are prepared for calibrating the detection equipment.

In the state of the art, a defective composite article is prepared with Teflon disks between the layers, and these disks serve to simulate the defects. Another kind of artificial defects known in the art is flat bottom holes drilled from the back side of the article to the depth in which the defect should present.

In recent years, new technologies, such as shearography and thermography are used for non-destructive detection of defects in composite articles, and these technologies also raise the need for novel calibration standards.

Some suggestions for composite articles with artificial defects other than Teflon disks or flat bottom holes are suggested in the following publications:

JP 10-22773 describes an artificial defect detection material for non-destructive inspection. The material has glass micro balls evenly distributed in a coupling base material. The glass micro balls include gas inside them.

JP 61265565 describes a method for forming standard flaw for non-destructive inspection. According to the described method a CFRP (carbon fiber reinforced plastic) plate is cut to two portions. Holes are accurately opened to one portion thereof by machining, and columns having the same diameters are cut from the other portion. The columns are finished by a grinding means so as to have diameters slightly smaller than the dimensions of the holes. Next, force is applied to the arbitrary place of each column to form layer delaminating to said column. This column having layer delaminating is sealed so as to prevent a resin such as an epoxy resin from penetrating into the layer delaminating parts from the circumference thereof. Subsequently, an adhesive equal to that used in the plate is applied to the periphery of the column after sealing and a coated column is inserted in each hole of the plate. In this case, a fiber direction is made same to attain to prevent abnormality from the aspect of flaw detection. Thereafter, the plate and the columns are finished so as to make both surfaces thereof flat to obtain a standard test piece.

SUMMARY OF THE INVENTION

According to the first aspect of the invention, there is provided a composite article comprising a plurality of layers, at least one of which being a defective polymeric layer. The defective polymeric layer has at least one artificial defect. The artificial defect is an air-filled void confined by walls made of the polymeric layer containing the defect, and by layers adjacent thereto. Therefore, a composite article according to the invention may be free of any foreign object that is aimed at holding the air in the composite, such as the glass micro-balls of JP 10-22773, the sealing used in JP 61265565, or the like.

According to one embodiment of the invention, a composite article according the invention is used for calibrating equipment that should detect, in a non-destructive manner, defects of predetermined size in a composite article. Non-limiting examples for technologies that such equipment may use are: shearography, thermography, ultrasound, and radiography.

Thus, the present invention provides a method for calibrating non-destructive detection equipment comprising detecting by said equipment defects in a calibration standard having defects of predetermined size; characterized in that said calibration standard is a composite article according to the present invention.

According another embodiment, a composite article according to the invention is used as a model for naturally defective composite article, for evaluating the damage tolerance of the naturally defective composite articles by methods that are, per se, known in the art. Such evaluation methods include application of static loads, or dynamic loads applied in a defined load spectrum (that is, in defined frequencies and amplitudes).

Thus, the present invention also provides a method for evaluating damage expected to be caused to a multilayered composite article under predetermined conditions, if it had a defect of predetermined characteristics. The method includes measuring the damage caused under such conditions to a second composite article, which is similar to the first composite article but has an artificial defect of the predetermined characteristics. The damage to be caused to the first composite article is evaluated to be the same as the damage caused to the second composite article. In accordance with the invention, the artificial defect of the second composite article is in the form of at least one air filled void in a polymeric layer, the void being confined by walls made of this polymeric layer, and by layers adjacent to it.

A composite article according to the invention includes a plurality of layers free of artificial defects (hereinafter non-defective layers) and at least one layer with artificial defect placed between them. The non-defective layers may be made of material that is the same as- or different from the material of the defective layer.

Non-limiting examples of materials, from which a layer of the composite article may be made, include polymers, metals, and ceramics. The polymers may be therpmoplastic or thermosetting in nature.

Non-limiting examples of possible polymers are resins and adhesives of epoxy, polyimides, polyolefins, phenolics, cyanate esters, and PEEK (polyetherether keton). Such polymers may be reinforced by fibers of carbon, glass, aramide, polyethylene or any other reinforcing fiber known in the art. The reinforcing fibers may have various forms known in the art, such as continuous and particulate (chopped).

Non-limiting examples of possible metals are aluminum, steel, and nickel-vanadium alloy. The metals may be bonded to polymers, non-limiting examples thereof are Kevlar® and Dyneema®.

Non-limiting examples of possible ceramics are alumina, silicon carbide, and boron carbide.

Artificial defects in a composite article of the invention may simulate defects of every known shape, and in particular, delamination, debonding, and porosity.

An artificial defect may be distinguished from a natural defect in that the artificial one has a regular shape.

Furthermore, when delamination is modeled, several artificial defects are positioned regularly inside the calibration standard, in difference from naturally occurring delaminations, that have non-regular positioning.

According to another aspect of the invention, it provides a method of making a composite article, having at least one artificial defect. The method of the invention includes bonding of a partially cured defective layer with a non-defective layer. According to one embodiment of the invention, the non-defective layer is also polymeric and partially cured. Preferably, the defective layer is bound to non-defective layers on both its sides.

The term curing is used herein to denote any process of toughening or hardening of a polymer material by crosslinking.

A polymer is said to be fully cured if it cannot be further cross-linked.

The degree of partial curing required from a partially cured layer according to the invention is such that the layer remains sticky, in order to allow it to be further cured and to allow its bonding with layers adjacent thereto. Additionally, at the temperature under which bonding with adjacent layers is carried out, all partially cured layers should have high enough viscosity to ensure that they do not penetrate (by flow or deformation) into the artificial defect.

The methods of the invention are designed to ensure that the hole made in the defective polymeric layer is not filled with resin during the bonding stage. Therefore, the size of the defect obtained at the end of the process is the same as the size of the hole made in the defective polymeric layer (within tolerance of about 10%). Thus, the invention provides for making composite articles with artificial defects of predetermined size.

According to another of its aspects, the present invention provides a partially cured polymeric layer with an artificial defect. Such layer may be used in a method according to the invention to make a composite article according to the invention. The artificial defect is an artificially made hole. Such hole may have dimensions of from about 1 mm to about 5cm. Holes that are used for simulating porosity are usually of a size of 1-3mm, and many of them present close to each other and preferably are positioned in a non-regular manner. Holes that are used for simulating delaminations are usually about 1-5cm in diameter.

According to one embodiment, a method according to the invention includes making at least one hole in a polymeric layer; partially curing the polymeric layer to obtain a sticky layer having a hole; and bonding the sticky layer to at least one non-defective layer. Preferably, before bonding the sticky layer to the non-defective layer, the hole is cleaned from resin that flowed into it during the partial curing.

According to another embodiment, the invented method includes partially curing a polymeric layer as to obtain a sticky layer; making a hole in the sticky layer; and bonding the sticky layer to at least one non-defective layer. In a preferred embodiment, the non-defective layer is polymeric, and it is also partially cured.

According to another aspect of the invention, there is provided a method of making a composite article having at least one artificial defect, the method comprising:
 (a) making at least one partially cured defective polymeric layer
 (b) making at least one partially cured non-defective polymeric layer; and
 (c) bonding together the partially cured defective polymeric layer and the partially cured non-defective polymeric layer.

According to one embodiment, a completely cured defective multilayer is obtained in (c); according to another embodiment, the multilayer obtained in (c) is partially cured, and the method also comprising bonding it with polymeric layers as to obtain a completely cured polymeric article.

Although the invented manufacturing process of the articles with artificial defects is divided into several stages, mechanical tests have shown that the mechanical properties of articles according to the invention comply with standard requirements for articles used for damage tolerance tests. Mechanical properties of calibration standards for non-destructive testing are not required to stand any specific standards.

BRIEF DESCRIPTION OF THE DRAWINGS

In order to understand the invention and to see how it may be carried out in practice, preferred embodiments will now be described, by way of non-limiting example only, with reference to the accompanying drawings, in which.

DETAILED DESCRIPTION OF THE INVENTION

Figure 1:
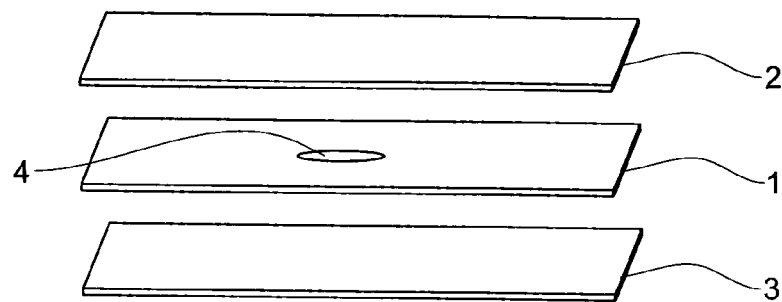
FIG. 1 is a schematic illustration of layers that together produce a composite article according to one embodiment of the invention.

In FIG. 1 there is shown a partially cured polymeric layer 1 given between two non-defective layers 2 and 3. The layer 1 is defective, in the sense that it includes an artificial defect 4. The defect 4 is circular, but in other embodiments similar defects may have any regular shape, such as square, oval, triangular, hexagonal, and the like. The defect 4 was cut in the layer 1 by a conventional cutting means (not shown), before partial curing. Cutting the layers to contain artificial defects may also be carried out after partial curing. The layers 1, 2, and 3 may be bonded together by heat pressing to form a calibration standard according to the invention.

According to a preferred embodiment, all the layers 1, 2, and 3 are made of partially cured graphite epoxy.

When more than one non-defective layer exists, each may be of a different material, similarly, when more than one defective layer exists, each may be of a different material.

According to another embodiment of the invention, the layer 1 is a partially cured polymeric adhesive, such as FM73 0,03psf by Cytec Fiberite, Havre DeGrase, MD21078, USA and the layers 2 and 3 are aluminum layers. The resultant calibration standard may be useful to simulate two aluminum layers adhered to each other with debonding area of the adhesive between them.

It should be noted, that in order to avoid deformation of any one of the layers 2 or 3 into the artificial defect 4, the layers 2 and 3 should be stable enough during bonding. In case of polymeric layers, this may require, that each of the layers 2 and 3 (and possibly also the defective layer 1) is by itself a multilayer, composed of several polymeric layers adhered to each other by partial curing.

Figure 2:
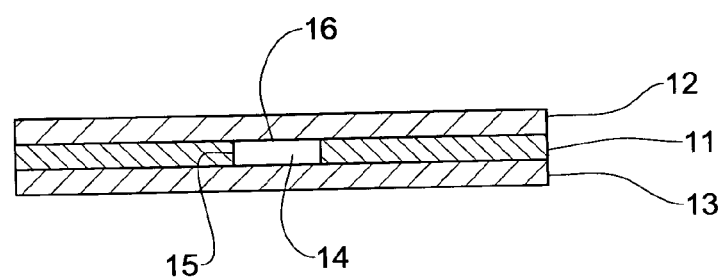
FIG. 2 is a cross-section in a portion of a composite article that may be produced from the layer of FIG. 1 by heat pressing them together.

FIG. 2 is a cross-section in a portion of a composite article 10 according to one embodiment of the invention. The article 10 includes three layers, 11, 12, and 13, of which layer 11 is defective. The defective layer 11 includes an air-filled void 14 having a circular wall 15 made of the polymeric defective layer 11 and walls 16 made of layers 12 and 13, which are adjacent to the defective layer 11.

Figure 3:
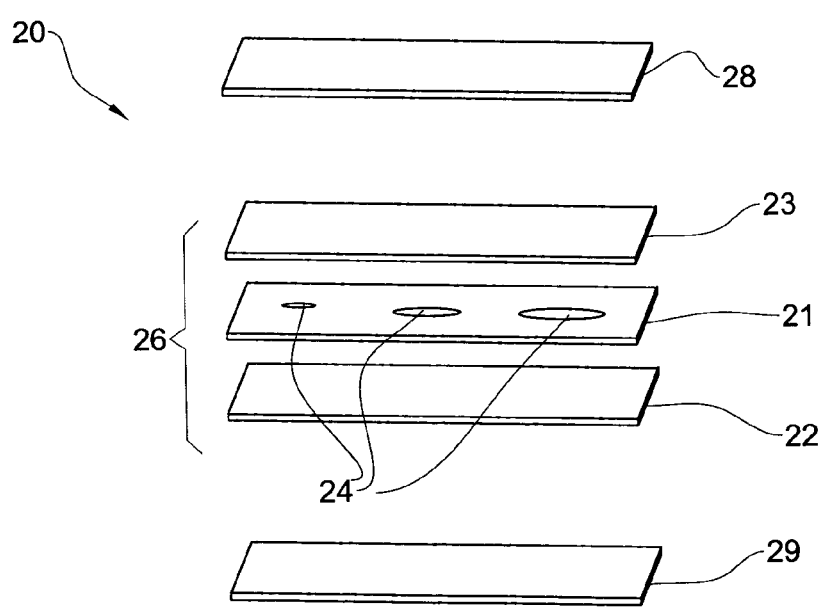
FIG. 3 is a cross-section in portion of composite article according to another embodiment of the invention.

According to one embodiment, shown in FIG. 3, a composite article 20 is prepared in four stages: in the first stage, layers 21, 22, and 23 are being partially cured to obtain three separate partially cured layers; in the second step, defects are cut in layer 21; in the third stage: the three partially cured layers are bonded together, and in the fourth stage, the resultant tri-layer 26 is further bonded to additional layers 28 and 29 that add to the thickness of the article 20.

The defects 24 illustrate one possibility of being regularly positioned within the article 20, as they are all in the same layer. The article 20 is particularly suitable as a calibration standard for non-destructive inspection. The defects 24 simulate delaminations of various sizes all in the same depth inside the article 20.

Figure 4:
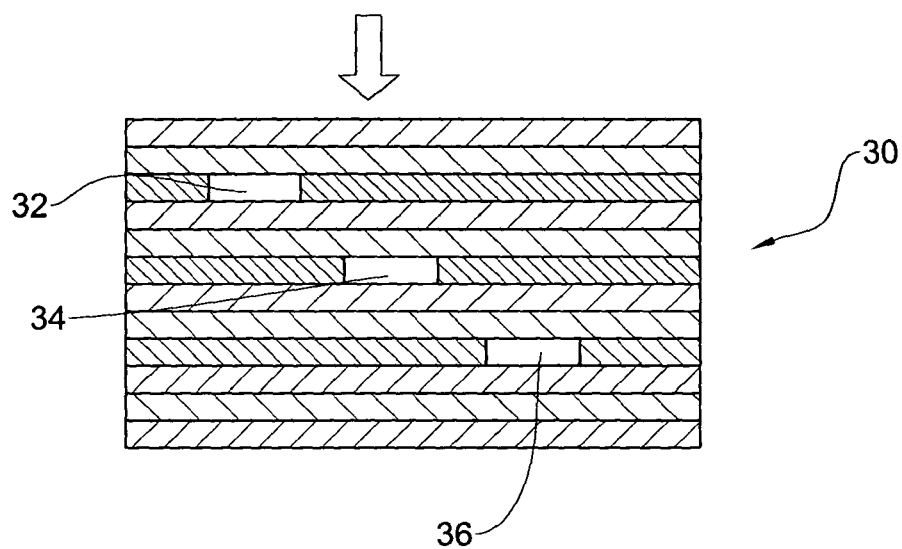
FIG. 4 is a schematic illustration of layers that together produce a composite article according to yet another embodiment of the invention.

FIG. 4 is a cross-section in a composite article 30 according to another embodiment of the invention, illustrating another possible regular positioning of defects. The article 30 has three artificial defects 32, 34, and 36 regularly positioned in the article. The defects 32, 34, and 36 are positioned each in a different layer, and they are arranged as not to hide each other from a spectator inspecting the article 30 from the direction of the arrow.

Naturally, FIGS. 3 and 4 do not exhaust the possibilities of regular positioning of defects in an article.

Figure 5:
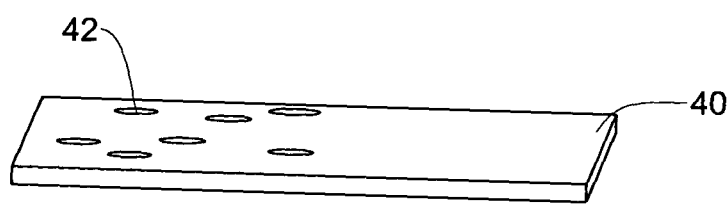
FIG. 5 is a schematic illustration of a layer useful in producing a composite article with artificial holes, for simulating a porosive article.

FIG. 5 shows a schematic illustration of a partially cured layer 40, having small defects 42, each having a diameter of about 1mm. One way to prepare such a defective layer is by drilling holes of about 1mm in diameter in a partially cured layer. Another way to prepare such a defected layer is by sticking into a prepreg a hot pin that upon being taken out of the prepreg leaves in it a hole, and than partially curing it.

Figure 6:
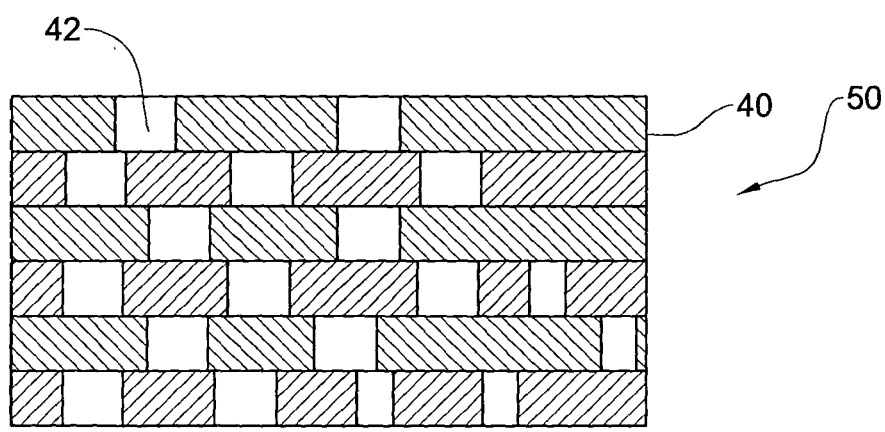
FIG. 6 is a cross-section in a portion a composite article that may be produced from layers such as illustrated in FIG. 5

FIG. 6 is a cross-section in a composite article 50 that may be obtained by bonding together a plurality of layers, similar to the one illustrated in FIG. 5. The article 50 has a variety of small defects in various depths, irregularly arranged as to simulate porosity.

MANUFACTURING EXAMPLE

Graphite epoxy composite W3T-282-F155 by Hexcel Composites 10 Trevarno Road, Livermore, Calif. 94550, USA with artificial defects was prepared as illustrated in FIG. 1 above. The defected layer 1 was prepared by cutting a layer of graphite epoxy by a punching device, and then treating the layer at 90° C. under pressure of 3.0 atmospheres for 100 min. The neighboring layers 2 and 3 were separately prepared in the same way, but without the cutting. Then, the layers 1, 2, and 3 were pressed together and treated at 130° C. under pressure of 3.0atm for 100 min.

The obtained composite article was tested by nondestructive means (ultrasound, digital shearography, and X-ray) and destructively, by microscopic investigation.

All tests proved that the article contained a defect (material deficiency) of a size that is substantially the same as the size of the defect artificially made in the layer 1, and the microscopic investigation also showed that the defect was an air filled void positioned at layer 1.

Mechanical tests have shown that the mechanical properties of the obtained article comply with standard requirements for articles used for damage tolerance tests.

We claim:

1. A method of making a composite article comprising a plurality of polymeric layers consisting of polymeric matrix and, optionally, fibers, said composite article having at least one artificial defect in the form of an air-filled void, the method comprising bonding polymeric layers to both sides of a partially cured sticky polymeric layer having an artificial defect in the form of an opening of a predetermined size and shape and having dimension of from 1 mm to 5 cm, thereby obtaining a composite article having at least one artificial defect in the form of an air-filled void confined by walls made by said polymeric layer containing the defect and by said polymeric layers adjacent thereto, the size and shape of said artificial defect in the composite article being of the predetermined size and shape of said opening.

2. A method according to claim 1, wherein said bonding is carried out by heat pressing.

3. A method according to claim 1, wherein said partially cured sticky polymeric layer having an artificial defect therein is made by:
   (a) making at least one hole in a polymeric layer; and
   partially curing said polymeric layer to obtain a sticky layer having a hole therein as said artificial defect.

4. A method according to claim 1, wherein said partially cured sticky polymeric layer having an artificial defect therein is made by:
   (a) partially curing a polymeric layer so as to obtain a sticky polymeric layer; and
   (b) making a hole in said sticky polymeric layer.

5. A method according to claim 1, wherein at least one of said polymeric layers bonded to either side of said polymeric layer having an artificial defect, is partially cured.

6. A method according to claim 1, wherein said polymeric layers consist of polymeric matrix and fibers.

7. A method according to claim 1, wherein at least one of said polymeric layers bonded to both sides of said polymeric layer having an artificial defect is a polymeric layer having no artificial defect therein.

* * * * *